United States Patent
Sasaki et al.

[11] 3,956,429
[45] May 11, 1976

[54] PHOSPHORYL PHENYLENEDIAMINES

[75] Inventors: Mitsuru Sasaki, Minoo; Kunio Mukai, Amagasaki; Katsutoshi Tanaka, Takarazuka, all of Japan

[73] Assignee: Sumitomo Chemical Company, Limited, Japan

[22] Filed: July 8, 1974

[21] Appl. No.: 486,510

[52] U.S. Cl.............. 260/944; 260/968; 424/211; 260/340.5
[51] Int. Cl.²............. C07F 9/24; A01N 9/36; C07D 317/06
[58] Field of Search............ 260/938, 340.5

[56] References Cited
UNITED STATES PATENTS

| | | | |
|---|---|---|---|
| 3,767,734 | 10/1973 | Mihailovski et al. | 260/938 X |
| 3,776,942 | 12/1973 | Miller et al. | 260/93 X |

*Primary Examiner*—Anton H. Sutto
*Attorney, Agent, or Firm*—Stewart and Kolasch, Ltd.

[57] ABSTRACT

A phenylenediamine compound of the formula:

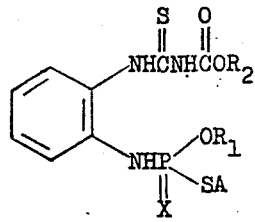

wherein $R_1$ is a lower alkyl group or a phenyl group which may bear one to five substituents, $R_2$ is a lower alkyl group, A is an alkyl group, an alkenyl group, an alkynyl group, a haloalkyl group, a phenyl group, a cyanoalkyl group, a lower alkylthioalkyl group, a haloalkenyl group, a lower alkoxyalkyl group, a lower alkoxycarbonylalkyl group, a lower alkylcarbamoylalkyl group or a phenylalkyl group which may bear one to five substituents on the benzene ring and X is an oxygen atom or a sulfur atom, which is useful as a pesticide effective in preventing and controlling simultaneously two or more kinds of plant diseases and can be produced by reacting an amidophosphoric ester of the formula:

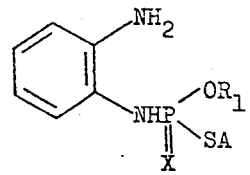

wherein $R_1$, A and X are each as defined above with an alkoxycarbonyl isothiocyanate of the formula:

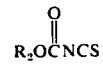

wherein $R_2$ is as defined above.

7 Claims, No Drawings

PHOSPHORYL PHENYLENEDIAMINES

The present invention relates to novel phenylenediamine compounds and their production and use.

The said phenylenediamine compounds are representable by the formula:

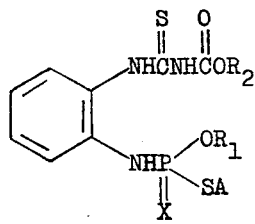

[I]

wherein $R_1$ is a lower alkyl group or a phenyl group which may bear one to five substituents, $R_2$ is a lower alkyl group, A is an alkyl group, an alkenyl group, an alkynyl group, a haloalkyl group, a phenyl group, a cyanoalkyl group, a lower alkylthioalkyl group, a haloalkenyl group, a lower alkoxyalkyl group, a lower alkoxycarbonylalkyl group, a lower alkylcarbamoylalkyl group or a phenylalkyl group which may bear one to five substituents on the benzene ring and X is an oxygen atom or a sulfur atom.

The term "lower" as herein used is intended to mean the one having not more than 8 (preferably not more than 5) carbon atoms. Any of the hydrocarbon residues or moieties such as alkyl, alkenyl or alkynyl may be a lower ($C_1$–$C_8$) or higher ($C_8$–$C_{30}$) one, when used without the term lower. The term "halogen" includes chlorine, bromine, iodine and fluorine. Examples of the substituents which may be present on the benzene ring are lower alkyl, lower alkoxy, lower alkylthio, nitro, cyano, halogen, lower alkylenedioxy, etc. Particularly preferred are lower alkyl, lower alkylthio, nitro, cyano and halogen for the substituents on the phenyl group represented by the symbol $R_1$ and lower alkyl, lower alkoxy, nitro, halogen and lower alkylenedioxy for the substituents on the phenyl group in the phenylalkyl group represented by the symbol A.

The phenylenediamine compounds [I] show a strong antimicrobial activity against a wide variety of microorganisms, particularly phytopathogenic bacteria and fungi including *Piricularia oryzae*, *Cochliobolus miyabeanus*, *Pellicularia sasakii*, *Sphaerotheca fulginea*, *Botrytic cinerea*, *Alternaria kikuchiana*, *Alternaria mali*, *Glomerella cingulata*, *Pythium aphanidermatum*, *Pellicularia filamentosa*, *Corticium rolfsii*, *Sclerotinia sclerotiorum*, *Aspergillus niger*, *Xanthomonas oryzae*, *Diaporthe citri*, *Colletotrichum lagenarium* and *Fusarium oxysporum f. lycopersici*, which cause plant diseases on crop plants, vegetables, flowers, fruit trees, etc. Advantageously, they exhibit an extremely low toxicity on mammals and do not cause any serious chemical injury on plants. In view of the meritorious characteristics as above, they are quite useful as pesticides which can prevent and control two or more kinds of plant diseases simultaneously.

According to the present invention, the phenylenediamine compounds [I] can be produced by reacting an amidophosphoric ester of the formula:

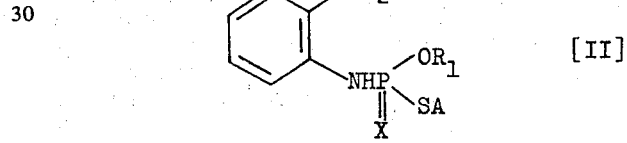

[II]

wherein $R_1$, A and X are each as defined above with an alkoxycarbonyl isothiocyanate of the formula:

[III]

wherein $R_2$ is as defined above.

The starting amidophosphoric ester [II] may be produced, for instance, by either one of the procedures as shown in the following scheme:

(A)

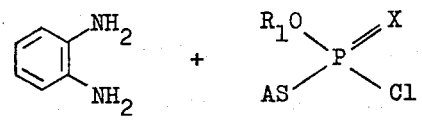

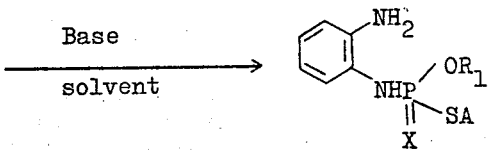

(B)

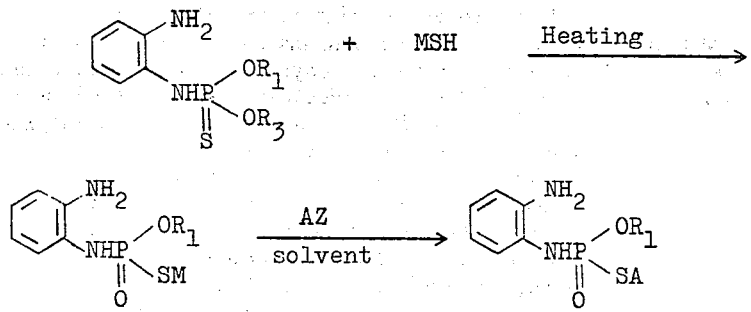

wherein $R_3$ is a lower alkyl group, M is an alkali metal atom, Z is a halogen atom and $R_1$, A and X are each as defined above.

Examples of the amidophosphoric ester [II] are as follows:

O,S-Dimethylphosphoryl-o-phenylenediamine;
O,S-Diethylphosphoryl-o-phenylenediamine;
O-Methyl-S-ethylphosphoryl-o-phenylenediamine;
O-Ethyl-S-methylphosphoryl-o-phenylenediamine;
O-Methyl-S-n-propylphosphoryl-o-phenylenediamine;
O-Methyl-S-n-butylphosphoryl-o-phenylenediamine;
O-Ethyl-S-n-propylphosphoryl-o-phenylenediamine;
O-Ethyl-S-isopropylphosphoryl-o-phenylenediamine;
O-Ethyl-S-n-butylphosphoryl-o-phenylenediamine;
O-Ethyl-S-sec.-butylphosphoryl-o-phenylenediamine;
O-Ethyl-S-n-amylphosphoryl-o-phenylenediamine;
O-Ethyl-S-benzylphosphoryl-o-phenylenediamine;
O-Ethyl-S-p-chlorobenzylphosphoryl-o-phenylenediamine;
O-Ethyl-S-p-tert.-butylbenzylphosphoryl-o-phenylenediamine;
O-Ethyl-S-p-bromobenzylphosphoryl-o-phenylenediamine;
O-Ethyl-S-p-nitrobenzylphosphoryl-o-phenylenediamine;
O-Methyl-S-benzylphosphoryl-o-phenylenediamine;
O-Methyl-S-2-phenethylphosphoryl-o-phenylenediamine;
O-Ethyl-S-2-phenethylphosphoryl-o-phenylenediamine;
O-Ethyl-S-3-phenylpropylphosphoryl-o-phenylenediamine;
O-Ethyl-S-2-methylthioethylphosphoryl-o-phenylenediamine;
O-Ethyl-S-2-chloroethylphosphoryl-o-phenylenediamine;
O-Ethyl-S-cyanomethylphosphoryl-o-phenylenediamine;
O-Ethyl-S-2-ethoxyethylphosphoryl-o-phenylenediamine;
O-Ethyl-S-ethoxycarbonylmethylphosphoryl-o-phenylenediamine;
O-Ethyl-S-methoxycarbonylmethylphosphoryl-o-phenylenediamine;
O-Ethyl-S-allylphosphoryl-o-phenylenediamine;
O-Methyl-S-alloylphosphoryl-o-phenylenediamine;
O-Ethyl-S-2-bromopropenylphosphoryl-o-phenylenediamine;
O-Ethyl-S-methallylphosphoryl-o-phenylenediamine;
O-Ethyl-S-propargylphosphoryl-o-phenylenediamine;
O-Methyl-S-proparagylphosphoryl-o-phenylenediamine;
O-Ethyl-S-phenylphosphoryl-o-phenylenediamine;
O-Methyl-S-p-tolylphosphoryl-o-phenylenediamine;
O-Methyl-S-2,4,5-trichlorophenylphosphoryl-o-phenylenediamine;
O-Ethyl-S-p-chlorophenylphosphoryl-o-phenylenediamine;
O-Ethyl-S-p-nitrophenylphosphoryl-o-phenylenediamine
O-Phenyl-S-methylphosphoryl-o-phenylenediamine;
O-p-Tolyl-S-methylphosphoryl-o-phenylenediamine;
O-p-Chlorophenyl-S-ethylphosphoryl-o-phenylenediamine;
O-p-Nitrophenyl-S-methylphosphoryl-o-phenylenediamine;
O-p-Methylthiophenyl-S-ethylphosphoryl-o-phenylenediamine;
O-p-Cyanophenyl-S-ethylphosphoryl-o-phenylenediamine;
O-Phenyl-S-phenylphosphoryl-o-phenylenediamine;
O,S-Dimethylthiophosphoryl-o-phenylenediamine;
O,S-Diethylthiophosphoryl-o-phenylenediamine;
O-Methyl-S-ethylthiophosphoryl-o-phenylenediamine;
O-Ethyl-S-methylthiophosphoryl-o-phenylenediamine;
O-Methyl-S-n-propylthiophosphoryl-o-phenylenediamine;
O-Methyl-S-n-butylthiophosphoryl-o-phenylenediamine;
O-Ethyl-S-n-propylthiophosphoryl-o-phenylenediamine;
O-Ethyl-S-isopropylthiophosphoryl-o-phenylenediamine;
O-Ethyl-S-n-butylthiophosphoryl-o-phenylenediamine;
O-Ethyl-S-sec.-butylthiophosphoryl-o-phenylenediamine;
O-Ethyl-S-n-amylthiophosphoryl-o-phenylenediamine;
O-Ethyl-S-benzylthiophosphoryl-o-phenylenediamine;
O-Ethyl-S-p-chlorobenzylthiophosphoryl-o-phenylenediamine;
O-Ethyl-S-p-tert.-butylbenzylthiophosphoryl-o-phenylenediamine;
O-Ethyl-S-p-bromobenzylthiophosphoryl-o-phenylenediamine;

O-Ethyl-S-p-nitrobenzylthiophosphoryl-o-phenylenediamine;
O-Methyl-S-benzylthiophosphoryl-o-phenylenediamine;
O-Methyl-S-2-phenethylphosphoryl-o-phenylenediamine;
O-Ethyl-S-2-phenethylphosphoryl-o-phenylenediamine;
O-Ethyl-S-3-phenylpropylthiophosphoryl-o-phenylenediamine;
O-Ethyl-S-2-methylthioethylphosphoryl-o-phenylenediamine;
O-Ethyl-S-2-chloroethylthiophosphoryl-o-phenylenediamine;
O-Ethyl-S-cyanomethylthiophosphoryl-o-phenylenediamine;
O-Ethyl-S-2-ethoxyethylthiophosphoryl-o-phenylenediamine;
O-Ethyl-S-ethoxycarbonylmethylthiophosphoryl-o-phenylenediamine;
O-Ethyl-S-methoxycarbonylmethylthiophosphoryl-o-phenylenediamine;
O-Ethyl-S-allylthiophosphoryl-o-phenylenediamine;
O-Methyl-S-allylthiophosphoryl-o-phenylenediamine;
O-Ethyl-S-2-bromopropenylthiophosphoryl-o-phenylenediamine;
O-Ethyl-S-methallylthiophosphoryl-o-phenylenediamine
O-Ethyl-S-propargylthiophosphoryl-o-phenylenediamine;
O-Methyl-S-propargylthiophosphoryl-o-phenylenediamine;
O-Ethyl-S-phenylthiophosphoryl-o-phenylenediamine;
O-Methyl-S-p-tolylthiophosphoryl-o-phenylenediamine;
O-Methyl-S-2,4,5-trichlorophenylthiophosphoryl-o-phenylenediamine;
O-Ethyl-S-p-chlorophenylthiophosphoryl-o-phenylenediamine;
O-Ethyl-S-p-nitrophenylthiophosphoryl-o-phenylenediamine;
O-Phenyl-S-methylthiophosphoryl-o-phenylenediamine;
O-p-Tolyl-S-methylthiophosphoryl-o-phenylenediamine;
O-p-Chlorophenyl-S-ethylthiophosphoryl-o-phenylenediamine;
O-p-Nitrophenyl-S-methylthiophosphoryl-o-phenylenediamine;
O-p-Methylthiophenyl-S-ethylthiophosphoryl-o-phenylenediamine;
O-p-Cyanophenyl-S-ethylthiophosphoryl-o-phenylenediamine;
O-Phenyl-S-phenylthiophosphoryl-o-phenylenediamine, etc.

Examples of the alkoxycarbonyl isothiocyanate [III] are methoxycarbonyl isothiocyanate, ethoxycarbonyl isothiocyanate, etc.

The reaction may be carried out by treatment of the amidophosphoric ester [II] with the alkoxycarbonyl isothiocyanate [III] in a non-polar solvent (e.g. benzene, toluene) at room temperature or while heating (preferably at a temperature of about 10° to 100°C), favorably under stirring to give the objective phenylenediamine compound [I] in an excellent yield.

Examples of the thus produced phenylenediamine compound [I] are shown in Table 1.

Table 1

| Compound No. | Chemical structure | M.P. (°C) |
|---|---|---|
| 1 | phenyl ring with NHC(S)NHC(O)OCH$_3$ and NHP(O)(OCH$_3$)(SCH$_3$) | 153–153.5 |
| 2 | phenyl ring with NHC(S)NHC(O)OCH$_3$ and NHP(O)(OC$_2$H$_5$)(SCH$_3$) | 124–125 |
| 3 | phenyl ring with NHC(S)NHC(O)OC$_2$H$_5$ and NHP(O)(OCH$_3$)(SCH$_3$) | 115–116 |
| 4 | phenyl ring with NHC(S)NHC(O)OC$_2$H$_5$ and NHP(O)(OC$_2$H$_5$)(SCH$_3$) | 121–122 |
| 5 | phenyl ring with NHC(S)NHC(O)OC$_2$H$_5$ and NHP(O)(OCH$_3$)(SC$_2$H$_5$) | 142.5 |

Table 1-continued

| Compound No. | Chemical structure | M.P. (°C) |
|---|---|---|
| 6 | 2-[NHC(S)NHCO₂C₂H₅]-C₆H₄-NHP(O)(OCH₃)(SC₃H₇(n)) | 152.5–153 |
| 7 | 2-[NHC(S)NHCO₂C₂H₅]-C₆H₄-NHP(O)(OCH₃)(SCH₂CH=CH₂) | 135–135.5 |
| 8 | 2-[NHC(S)NHCOCH₃]-C₆H₄-NHP(O)(OC₂H₅)(SC₂H₅) | 160–161 |
| 9 | 2-[NHC(S)NHCOC₂H₅]-C₆H₄-NHP(O)(OC₂H₅)(SC₂H₅) | 162 |
| 10 | 2-[NHC(S)NHCOC₂H₅]-C₆H₄-NHP(O)(OC₂H₅)(SC₃H₇(n)) | 162–162.5 |
| 11 | 2-[NHC(S)NHCOC₂H₅]-C₆H₄-NHP(O)(OC₂H₅)(SC₃H₇(iso)) | 158–158.5 |
| 12 | 2-[NHC(S)NHCOC₂H₅]-C₆H₄-NHP(O)(OC₂H₅)(SC₄H₉(n)) | 156–156.5 |
| 13 | 2-[NHC(S)NHCOC₂H₅]-C₆H₄-NHP(O)(OC₂H₅)(SC₅H₁₁(n)) | 152.5–153.5 |
| 14 | 2-[NHC(S)NHCOC₂H₅]-C₆H₄-NHP(O)(OC₂H₅)(SC₄H₉(sec)) | 151–152 |
| 15 | 2-[NHC(S)NHCOC₂H₅]-C₆H₄-NHP(O)(OC₂H₅)(SCH₂CH=CH₂) | 151–151.5 |

Table 1-continued

| Compound No. | Chemical structure | M.P. (°C) |
|---|---|---|
| 16 | 2-[NHC(S)NHCOC$_2$H$_5$]-C$_6$H$_4$-NHP(O)(OC$_2$H$_5$)(SCH$_2$C≡CH) | 143–145 |
| 17 | 2-[NHC(S)NHCOC$_2$H$_5$]-C$_6$H$_4$-NHP(O)(OC$_2$H$_5$CH$_3$)(SCH$_2$C=CH$_2$) | 149–149.5 |
| 18 | 2-[NHC(S)NHCOC$_2$H$_5$]-C$_6$H$_4$-NHP(O)(OC$_2$H$_5$)(SCH$_2$-C$_6$H$_5$) | 161–161.5 |
| 19 | 2-[NHC(S)NHCOC$_2$H$_5$]-C$_6$H$_4$-NHP(O)(OC$_2$H$_5$)(SCH$_2$-C$_6$H$_4$-Cl) | 181–182 |
| 20 | 2-[NHC(S)NHCOC$_2$H$_5$]-C$_6$H$_4$-NHP(O)(OC$_2$H$_5$)(SCH$_2$-C$_6$H$_4$-C$_4$H$_9$(tert)) | 140–142 |
| 21 | 2-[NHC(S)NHCOC$_2$H$_5$]-C$_6$H$_4$-NHP(O)(OC$_2$H$_5$)(SCH$_2$CH$_2$-C$_6$H$_5$) | 134–134.5 |
| 22 | 2-[NHC(S)NHCOC$_2$H$_5$]-C$_6$H$_4$-NHP(O)(OC$_2$H$_5$)(SCH$_2$COOC$_2$H$_5$) | 115–116 |
| 23 | 2-[NHC(S)NHCOC$_2$H$_5$]-C$_6$H$_4$-NHP(O)(OC$_2$H$_5$)(SCH$_2$CH$_2$SCH$_3$) | 168 |
| 24 | 2-[NHC(S)NHCOC$_2$H$_5$]-C$_6$H$_4$-NHP(O)(OC$_2$H$_5$)(SCH$_2$CH$_2$OC$_2$H$_5$) | 155.5–156 |

Table 1-continued

| Compound No. | Chemical structure | M.P. (°C) |
|---|---|---|
| 25 | 2-[NHC(S)NHC(O)OC$_2$H$_5$]-C$_6$H$_4$-NHP(O)(OC$_2$H$_5$)(SCH$_2$-(2,4-(CH$_3$)$_2$C$_6$H$_3$)) | 163–163.5 |
| 26 | 2-[NHC(S)NHC(O)OC$_2$H$_5$]-C$_6$H$_4$-NHP(O)(OC$_2$H$_5$)(SCH$_2$-(3-ClC$_6$H$_4$)) | 157.5–158 |
| 27 | 2-[NHC(S)NHC(O)OC$_2$H$_5$]-C$_6$H$_4$-NHP(O)(OC$_2$H$_5$)(SCH$_2$-(2-ClC$_6$H$_4$)) | 161–162 |
| 28 | 2-[NHC(S)NHC(O)OC$_2$H$_5$]-C$_6$H$_4$-NHP(O)(OC$_2$H$_5$)(SCH$_2$-(4-BrC$_6$H$_4$)) | 173.5–174 |
| 29 | 2-[NHC(S)NHC(O)OC$_2$H$_5$]-C$_6$H$_4$-NHP(O)(OC$_2$H$_5$)(SCH$_2$-(4-CH$_3$C$_6$H$_4$)) | 160.5–161 |
| 30 | 2-[NHC(S)NHC(O)OC$_2$H$_5$]-C$_6$H$_4$-NHP(O)(OC$_2$H$_5$)(SCH$_2$-(2,4-(CH$_3$)$_2$C$_6$H$_3$)) | 161–161.5 |
| 31 | 2-[NHC(S)NHC(O)OC$_2$H$_5$]-C$_6$H$_4$-NHP(O)(OC$_2$H$_5$)(SCH$_2$SCH$_3$) | 144.5–145 |
| 32 | 2-[NHC(S)NHC(O)OC$_2$H$_5$]-C$_6$H$_4$-NHP(O)(OC$_2$H$_5$)(SCH$_2$-(4-iso-C$_3$H$_7$C$_6$H$_4$)) | 161.5–162 |

Table 1-continued

| Compound No. | Chemical structure | M.P. (°C) |
|---|---|---|
| 33 | 2-[NHC(S)NHC(O)CH₃]-C₆H₄-NHP(O)(OCH₃)(SCH₂C₆H₅) | 161.5–162 |
| 34 | 2-[NHC(S)NHC(O)C₂H₅]-C₆H₄-NHP(O)(OC₂H₅)(SCH₂COOC₃H₇(iso)) | 78–79 |
| 35 | 2-[NHC(S)NHC(O)C₂H₅]-C₆H₄-NHP(O)(OC₂H₅)(SC₅H₁₁(iso)) | 161–161.5 |
| 36 | 2-[NHC(S)NHC(O)C₂H₅]-C₆H₄-NHP(O)(OC₂H₅)(SC₆H₁₃(n)) | 127–127.5 |
| 37 | 2-[NHC(S)NHC(O)C₂H₅]-C₆H₄-NHP(O)(OC₂H₅)(SC₇H₁₅(n)) | 120–121 |
| 38 | 2-[NHC(S)NHC(O)C₂H₅]-C₆H₄-NHP(O)(OC₂H₅)(SC₈H₁₇(n)) | 114–114.5 |
| 39 | 2-[NHC(S)NHC(O)C₂H₅]-C₆H₄-NHP(O)(OC₂H₅)(SC₉H₁₉(n)) | 108–108.5 |
| 40 | 2-[NHC(S)NHC(O)C₂H₅]-C₆H₄-NHP(O)(OC₂H₅)(SCH₂-C₆H₄-3-F) | 155–155.5 |
| 41 | 2-[NHC(S)NHC(O)C₂H₅]-C₆H₄-NHP(O)(OC₂H₅)(SCH₂-C₆H₄-3-CH₃) | 161–161.5 |

Table 1-continued

| Compound No. | Chemical structure | M.P. (°C) |
|---|---|---|
| 42 | 2-[NHC(S)NHC(O)OC$_2$H$_5$]-C$_6$H$_4$-NHP(O)(OC$_2$H$_5$)(SCH$_2$-C$_6$H$_4$-3-OCH$_3$) | 133–134 |
| 43 | 2-[NHC(S)NHC(O)OC$_2$H$_5$]-C$_6$H$_4$-NHP(O)(OC$_2$H$_5$)(SCH$_2$-C$_6$H$_4$-4-OCH$_3$) | 165.5–166.5 |
| 44 | 2-[NHC(S)NHC(O)OC$_2$H$_5$]-C$_6$H$_4$-NHP(O)(OC$_2$H$_5$)(SCH$_2$-C$_6$H$_3$-3,4-Cl$_2$) | 184–185 |
| 45 | 2-[NHC(S)NHC(O)OC$_2$H$_5$]-C$_6$H$_4$-NHP(O)(OC$_2$H$_5$)(SCH$_2$-C$_6$H$_3$-2,4-Cl$_2$) | 160–161.5 |
| 46 | 2-[NHC(S)NHC(O)OC$_2$H$_5$]-C$_6$H$_4$-NHP(O)(OC$_2$H$_5$)(SC$_{10}$H$_{21}$(n)) | 101–101.5 |
| 47 | 2-[NHC(S)NHC(O)OC$_2$H$_5$]-C$_6$H$_4$-NHP(O)(OC$_2$H$_5$)(SC$_{11}$H$_{23}$(n)) | 94.5–95.5 |
| 48 | 2-[NHC(S)NHC(O)OC$_2$H$_5$]-C$_6$H$_4$-NHP(O)(OC$_2$H$_5$)(SC$_{12}$H$_{25}$(n)) | 92–92.5 |
| 49 | 2-[NHC(S)NHC(O)OC$_2$H$_5$]-C$_6$H$_4$-NHP(O)(OC$_2$H$_5$)(SCH$_2$-C$_6$H$_4$-2-F) | 141–142 |

Table 1-continued

| Compound No. | Chemical structure | M.P. (°C) |
|---|---|---|
| 50 | 2-[NHC(S)NHC(O)OC$_2$H$_5$]-C$_6$H$_4$-NHP(O)(OC$_2$H$_5$)(SCH$_2$-(1,3-benzodioxol-5-yl)) | 158–160 |
| 51 | 2-[NHC(S)NHC(O)OC$_2$H$_5$]-C$_6$H$_4$-NHP(O)(OC$_2$H$_5$)(SCH$_2$-C$_6$H$_4$-4-C$_2$H$_5$) | 139–140 |
| 52 | 2-[NHC(S)NHC(O)OC$_2$H$_5$]-C$_6$H$_4$-NHP(O)(OC$_2$H$_5$)(SCH$_2$-C$_6$H$_4$-4-F) | 180.5–181 |
| 53 | 2-[NHC(S)NHC(O)OC$_2$H$_5$]-C$_6$H$_4$-NHP(O)(OC$_2$H$_5$)(SCH$_2$-C$_6$H$_4$-2-CH$_3$) | 153–154 |
| 54 | 2-[NHC(S)NHC(O)OC$_2$H$_5$]-C$_6$H$_4$-NHP(O)(OC$_2$H$_5$)(SC$_{16}$H$_{33}$(n)) | 93.5–94.5 |
| 55 | 2-[NHC(S)NHC(O)OC$_2$H$_5$]-C$_6$H$_4$-NHP(O)(OC$_2$H$_5$)(SCH$_2$COOC$_4$H$_9$(iso)) | 98–98.5 |
| 56 | 2-[NHC(S)NHC(O)OC$_2$H$_5$]-C$_6$H$_4$-NHP(O)(OCH$_3$)(SC$_4$H$_9$(n)) | 136–136.5 |
| 57 | 2-[NHC(S)NHC(O)OC$_2$H$_5$]-C$_6$H$_4$-NHP(O)(OCH$_3$)(SC$_6$H$_{13}$(n)) | 152.5–153.5 |

Table 1-continued

| Compound No. | Chemical structure | M.P. (°C) |
|---|---|---|
| 58 | (structure) | 133-135 |
| 59 | (structure) | 160-160.5 |
| 60 | (structure) | 92.5-93.5 |
| 61 | (structure) | 40-43 |
| 62 | (structure) | 138-140 |

Some practical procedures for the preparation of the phenylenediamine compounds [I] are shown in the following Examples.

EXAMPLE 1

To a suspension of o-phenylenediamine (0.1 mol) in 20% aqueous solution of sodium hydroxide, O,O-dimethylthio-phosphoryl chloride (0.1 mol) is dropwise added at room temperature, and stirring is continued for a while. When the reaction mixture is made acidic, it is extracted with benzene. The benzene extract is washed with water and dried. On removal of the benzene by distillation under reduced pressure, there is obtained O,O-dimethylthiophosphoryl-o-phenylenediamine (M.P. 71° – 72°C) in a yield of 85%.

EXAMPLE 2

O,O-Diethylthiophosphoryl-o-phenylenediamine (0.1 mol) prepared as in Example 1 is dropwise added to a solution of sodium hydrosulfide (0.1 mol) in methylcellosolve. The resulting mixture is kept at 105° to 110°C for 5 hours and then the methylcellosolve is distilled off. To the residue, benzene and water are added, and the water layer is separated from the benzene layer, washed with benzene and concentrated. The resulting sodium salt is dissolved in ethanol, an equimolar amount of ethyl iodide is added thereto and the resultant mixture is maintained at 80°C for 1 hour. After removal of the ethanol, the residue is extracted with benzene and the benzene extract is washed with water, dried and concentrated to give O,S-diethylphosphoryl-o-phenylenediamine (M.P. 60° – 62°C) in a yield of 81%. This product is dissolved in benzene, and an equimolar amount of ethoxycarbonyl isothiocyanate is added thereto. The precipitated crystals are collected by filtration to give N-O,S-diethylphosphoryl-N'-ethoxycarbonylthioureido-o-phenylenediamine (M.P. 162°C) in a yield of 95%.

EXAMPLE 3

To a solution of o-phenylenediamine (0.1 mol) in ether, O-ethyl-S-n-propylphosphoryl chloride (0.1 mol) is added, and triethylamine (0.1 mol) is dropwise added thereto at a temperature below 10°C. The resulting mixture is stirred at room temperature for 3 hours. The reaction mixture is washed with water and the ether is distilled off. The resultant brown oil is dissolved in benzene, an equimolar amount of ethoxycarbonyl isothiocyanate is added thereto, and the resultant mixture is allowed to stand overnight. The precipitated crystals are collected by filtration and recrystallized from a mixture of benzene and n-hexane to give N-O-ethyl-S-n-propylphosphoryl-N'-ethoxycarbonylthioureido-o-phenylenediamine (M.P. 162° – 162.5°C) in a yield of 85%.

EXAMPLE 4

O-Ethyl-S-ethoxycarbonylmethylphosphoryl-o-phenylenediamine (0.1 mol) prepared as in Example 2 is dissolved in a small amount of benzene, and an equimolar amount of ethoxycarbonyl isothiocyanate is added thereto. After several minutes, there are precipitated crystals, which are collected by filtration to give N-O-ethyl-S-ethoxycarbonylmethylphosphoryl-N'-ethoxycarbonyl-thioureido-o-phenylenediamine (M.P. 115° – 116°C) in a yield of 93%.

In the same manner as above, other phenylenediamine compounds as shown in Table 1 can be produced.

As the pesticide, the phenylenediamine compound [I] may be used alone. For the practical use, however, it is usually extended with a suitable carrier or diluent, if desired, by the aid of any emulsifier to formulate a preparation as conventionally employed in this art field such as pellets, dust, wettable powder or emulsifiable concentrate.

Examples of the solid carrier or diluent are talc, bentonite, clay, kaolin, diatomaceous earth, vermiculite, calcium hydroxide, etc. Examples of the liquid carrier or diluent are benzene, alcohols, acetone, xylene, dioxane, methylnaphthalene, cyclohexane, etc. As the emulsifier, there may be employed alkylsulfates, alkylsulfonates, arylsulfonates, polyethyleneglycol ethers, polyvalent alcohol esters and the like.

When desired, the preparation may contain any other active ingredient such as a fungicide, an insecticide, a lanatocide, a herbicide or a fertilizer.

Some specific embodiments of the preparation comprising the phenylenediamine compound [I] as the active ingredient are shown in the following Examples wherein parts and % are by weight.

EXAMPLE A

Dust

The phenylenediamine compound [I] (e.g. Compound No. 1 in Table 1) (2 parts) and clay (98 parts) are pulverized and mixed well to make a dust comprising the active ingredient in a concentration of 2%. The dust may be applied as such or admixed with soil on use.

EXAMPLE B

Dust

The phenylenediamine compound [I] (e.g. Compound No. 4 in Table 1) (3 parts) and talc (97 parts) are pulverized and mixed well to make a dust comprising the active ingredient in a concentration of 3%. The dust may be applied as such or admixed with soil on use.

EXAMPLE C

Wettable powder

The phenylenediamine compound [I] (e.g. Compound No. 9 in Table 1) (50 parts), a wetting agent (alkylbenzenesulfonate) (5 parts) and diatomaceous earth (45 parts) are pulverized and mixed well to make a wettable powder comprising the active ingredient in a concentration of 50%. The wettable powder may be diluted with water and then applied on use.

EXAMPLE D

Emulsifiable concentrate

The phenylenediamine compound [I] (e.g. Compound No. 20 in Table 1) (10 parts), an emulsifier (polyoxyethylene phenylphenol ether) (10 parts) and dimethylsulfoxide (80 parts) are mixed well to make an emulsifiable concentrate comprising the active ingredient in a concentration of 10%. The emulsifiable concentrate may be applied as such or after dilution with water on use.

EXAMPLE E

Pellets

The phenylenediamine compound [I] (e.g. Compound No. 3 in Table 1) (5 parts), clay (93.5 parts) and a binding agent (polyvinyl alcohol) (1.5 parts) are pulverized and mixed well. The resulting mixture is kneaded with water, pelletized and dried to give pellets comprising the active ingredient in a concentration of 5%. The pellets may be applied as such on use.

EXAMPLE F

Composite dust

The phenylenediamine compound [I] (e.g. Compound No. 47 in Table 1) (2 parts), O-n-butyl-S-ethyl-S-benzyl-phosphorodithiolate (1.5 parts) and clay (96.5 parts) are pulverized and mixed well to make a dust comprising the active ingredients in a concentration of 3.5%. The dust may be applied as such on use.

EXAMPLE G

Composite dust

The phenylenediamine compound [I] (e.g. Compound No. 4 in Table 1) (2 parts), Kasugamycin (0.1 part), O,O-dimethyl-O-(3-methyl-4-nitrophenyl)phosphorothioate (2 parts), 3,4-dimethylphenyl-N-methylcarbamate (1.5 parts) and clay (95 parts) are pulverized and mixed well to make a dust comprising the active ingredients in a concentration of 5%. The dust may be applied as such on use.

EXAMPLE H

Composite dust

The phenylenediamine compound [I] (e.g. Compound No. 22 in Table 1) (2 parts), N-(3',5'-dichlorophenyl)succinimide (1.5 parts), O,O-dimethyl-O-(3-methyl-4-nitrophenyl)phosphorothioate (2 parts), 3,4-dimethylphenyl-N-methylcarbamate (1.5 parts) and clay (93 parts) are pulverized and mixed well to make a dust comprising the active ingredients in a concentration of 7%. The dust may be applied as such on use.

EXAMPLE I

Composite wettable powder

The phenylenediamine compound [I] (e.g. Compound No. 5 in Table 1) (30 parts), zinc ethylenebisdithiocarbamate (10 parts), 1,2-bis[(3-methoxycarbonyl)thioureido]benzene (10 parts), calcium alkylbenzenesulfonate (5 parts) and diatomaceous earth (45 parts) are pulverized and mixed well to make a wettable powder comprising the active ingredients in a concentration of 50%. The wettable powder may be diluted with water and then applied on use.

The following test data support that the phenylenediamine compounds [I] have a more excellent antimicrobial activity than known commercially available pesticides and are effective in preventing and controlling multi plant diseases:

Test 1

Growth inhibitory effects on microorganisms

The growth inhibitory potency of the phenylenediamine compounds [I] on five kinds of phytopathogenic microorganisms was examined according to the agar dilution method. The evaluation was made on the following criteria:

A. Complete inhibition at a concentration of 50 ppm
B. Inhibition to less than 5% at a concentration of 50 ppm in comparison with the control (untreated)
C. Inhibition to less than 10% at a concentration of 50 ppm in comparison with the control
D. Inhibition to less than 20% at a concentration of 50 ppm in comparison with the control
E. Inhibition to less than 50% at a concentration of 50 ppm in comparison with the control
F. No inhibition at a concentration of 50 ppm The results are shown in Table 2 wherein the abbreviations have the following meanings:
Cm — *Cochliobolus miyabeanus*
Gc — *Glomerella cingulata*
Ss — *Sclerotinia sclerotiorum*
Cl — *Colletotrichum lagenarium*
Bc — *Botrytis cinerea*

Table 2

| Compound No. | Cm | Gc | Ss | Cl | Bc |
|---|---|---|---|---|---|
| 1 | A | A | B | A | A |
| 2 | B | A | A | A | B |
| 3 | B | A | A | A | A |
| 4 | A | A | A | A | A |
| 5 | C | A | A | A | A |
| 7 | B | A | A | A | B |
| 8 | B | B | A | A | A |
| 9 | B | A | A | A | A |
| 10 | C | A | A | A | A |
| 14 | B | A | B | A | A |
| 19 | B | A | B | A | A |
| 20 | A | A | B | A | B |
| 23 | B | A | B | A | B |
| 24 | B | A | A | A | B |
| 25 | B | A | B | A | B |
| 27 | B | A | A | A | B |
| 28 | A | A | A | A | B |
| 29 | B | B | A | A | A |
| 30 | B | A | A | A | B |
| 32 | A | A | B | A | A |
| 33 | B | A | B | A | A |
| 36 | B | A | B | A | A |
| 39 | C | A | B | A | B |
| 40 | B | A | B | A | A |
| 43 | B | A | A | A | B |
| 44 | B | A | A | A | B |
| 45 | B | A | A | A | B |
| 49 | B | A | A | A | B |
| 50 | B | A | A | A | A |
| 51 | B | A | A | A | A |

Table 2-continued

| Compound No. | Cm | Gc | Ss | Cl | Bc |
|---|---|---|---|---|---|
| 53 | B | A | A | A | A |
| 55 | B | A | A | A | B |

Test 2

Growth inhibitory effects on microorganisms

The growth inhibitory potency of the phenylenediamine compounds [I] on nine kinds of phytopathogenic microorganisms was examined according to the agar dilution method. The evaluation was made on the following criteria:

A. Complete inhibition at a concentration of 25 ppm
B. Inhibition to less than 10% at a concentration of 25 ppm
C. Inhibition to less than 20% at a concentration of 25 ppm The results are shown in Table 3 wherein the abbreviations have the following meanings:
Dc — *Diaporthe citri*
Ps — *Pellicularia sasakii*
Po — *Pyricularia oryzae*
Xo — *Xanthomonas oryzae*
Fol — *Fusarium oxysporum f. lycopersici*
Gc, Ss, Bc, Cl — Same as in Test 1.

Table 3

| Compound No. | Gc | Ss | Dc | Ps | Cl | Bc | Po | Xo | Fol |
|---|---|---|---|---|---|---|---|---|---|
| 1 | A | A | A | A | A | A | A | B | A |
| 2 | A | A | B | A | A | A | A | A | B |
| 3 | A | A | A | A | A | A | A | C | B |
| 4 | A | A | A | A | A | A | A | A | A |
| 5 | A | A | A | B | A | A | A | B | A |
| 6 | A | A | A | B | A | A | A | C | B |
| 7 | A | A | A | A | B | A | A | C | A |
| 8 | A | A | A | A | A | A | A | A | A |
| 9 | A | A | A | A | A | A | A | C | A |
| 11 | A | A | A | B | A | A | A | C | A |
| 16 | A | A | A | B | B | A | A | B | B |
| 31 | A | A | A | A | A | A | B | C | A |
| 32 | A | A | A | B | A | A | B | C | A |
| 33 | A | A | A | A | A | A | A | B | B |
| 34 | A | A | A | A | A | A | A | B | B |
| 35 | A | A | A | A | B | A | B | A | A |
| 41 | A | A | A | A | A | B | B | A | A |
| 47 | A | A | A | B | A | B | A | A | B |
| 51 | A | A | A | B | A | A | A | C | A |
| 56 | A | A | A | A | A | B | B | C | A |
| 62 | A | A | A | A | A | A | A | B | B |

Test 3

Rice blast controlling effects

The test compound in the form of an emulsifiable concentrate preparation was applied to rice plants cultured in pots of 9 cm in diameter and grown up to the five leaved stage at a rate of 10 ml of the preparation per pot by the use of a spray gun. After 24 hours, the plants were sprayed to inoculate thereon with a spore suspension of Pyricularia oryzae cultured in an oatmeal medium. The plants were placed in a room of high humidity at 26°C. Three days thereafter, the degree of damage was determined based on the percentage of the infectious area, and the degree of damage and the degree of disease-preventing effect were calculated according to the following equations, respectively:

$$\text{Degree of damage} = \frac{\Sigma(\text{Infectious index} \times \text{Number of leaves})}{\text{Total number of leaves} \times 5} \times 100$$

wherein the infectious index was determined by the following criteria:

| Infectious index | Infectious state |
| --- | --- |
| 0 | No infectious spot |
| 1 | Infectious spots only at or around the inoculated place |
| 2 | Infectious spots in about one fifth of the inoculated leaf |
| 3 | Infectious spots in about two fifths of the inoculated leaf |
| 4 | Infectious spots in about three fifths of the inoculated leaf |
| 5 | Infectious spots in four fifths or more of the inoculated leaf |

Degree of disease-preventing effect =

$$\frac{\left(\begin{array}{c}\text{Number of infectious spots}\\ \text{in untreated plot}\end{array}\right) - \left(\begin{array}{c}\text{Number of infectious}\\ \text{spots in treated plot}\end{array}\right)}{\text{Number of infectious spots in untreated plot}} \times 100$$

The results are shown in Table 4 wherein the commercially available fungicide is O,O-diisopropyl-S-benzyl-thiophosphate.

Table 4

| Compound No. | Concentration (ppm) | Degree of damage (%) | Degree of disease-preventing effect | Chemical injury |
| --- | --- | --- | --- | --- |
| 1 | 500 | 0 | 100 | None |
| 3 | 500 | 1.0 | 99 | " |
| 4 | 500 | 0 | 100 | " |
| 6 | 500 | 2.0 | 98 | " |
| 12 | 500 | 3.5 | 96 | " |
| 13 | 500 | 4.0 | 96 | " |
| 15 | 500 | 3.5 | 96 | " |
| 20 | 500 | 0 | 100 | " |
| 21 | 500 | 0 | 100 | " |
| 22 | 500 | 1.0 | 99 | " |
| 26 | 500 | 1.0 | 99 | " |
| 34 | 500 | 1.0 | 99 | " |
| 37 | 500 | 2.0 | 98 | " |
| 41 | 500 | 3.0 | 97 | " |
| 46 | 500 | 3.0 | 97 | " |
| 48 | 500 | 0 | 100 | " |
| 51 | 500 | 4.0 | 96 | " |
| 55 | 500 | 2.0 | 98 | " |
| 58 | 500 | 3.5 | 96 | " |
| 59 | 500 | 1.0 | 99 | " |
| Commercially available fungicide | 200 | 5.5 | 94 | " |
| Untreated | — | 100.0 | — | " |

Test 4

Rice blast controlling effects (in field)

Rice plants were cultured in the field (each plot having an area of 1 m²) and, when grown up to the three to four leaved stage, straw infected with Pyricularia oryzae was placed between the stems for inoculation. When initial infectious spots were recognized, the test compound in the form of a dust preparation was sprayed on the rice plants at a rate of 4 kg per 10 are. After 7 days, the second application was carried out in the same manner as above. Ten days after the second application, the first observation was made on 25 stocks in each of the plots. The second and third observations were made at intervals of 10 days. The results are shown in Table 5 wherein the commercially available fungicides A and B are 4,5,6,7-tetrachlorophthalide and O,O-diisopropyl-S-benzyl-thiophosphate.

Table 5

| Compound No. | Concentration | Rate of infectious area in average (%) | | | Chemical injury |
| --- | --- | --- | --- | --- | --- |
| | | 1st | 2nd | 3rd | |
| 4 | 3 % (dust) | 9.69 | 20.95 | 30.85 | None |
| Commercially available fungicide A | 3 % (dust) | 12.91 | 13.40 | 20.97 | " |
| Commercially available fungicide B | 48 % (emulsion)* | 15.81 | 29.89 | 70.95 | " |
| Untreated | — | 32.35 | 63.35 | 92.22 | " |

*Applied in a rate of 150 liters per 10 are.

Test 5

Sheath blight controlling effects

The test compound in the form of a wettable powder preparation was applied to rice plants cultured in pots of 9 cm in diameter and grown up to 60 cm tall at a rate of 10 ml of the preparation per pot by the use of a spray gun. After 24 hours, a mycelium-disc-inoculum (5 mm in diameter) of Pellicularia sasakii cultured on PS synthetic medium was inoculated on the sheath, and the plants were placed into a room at 28°C. Four days thereafter, the infectious state at the sheath was observed, and the size of the diseased spot was measured. The degree of damage and the degree of disease-preventing effect of the test compound were calculated according to the following equations, respectively:

$$\text{Degree of damage} = \frac{\Sigma(\text{Infectious index} \times \text{Number of stems})}{\text{Total number of stems} \times 3} \times 100$$

wherein the infectious index was determined on the following criteria:

| Infectious index | Infectious state |
| --- | --- |
| 0 | No infectious spots on sheath |
| 1 | Infectious spot-like parts |
| 2 | Infectious spots of less than 3 cm in size |
| 3 | Infectious spots of not less than |

| Infectious index | Infectious state |
| --- | --- |
| | 3 cm in size |

Degree of disease-preventing effect =

$$\frac{\left(\begin{array}{c}\text{Degree of damage in}\\\text{untreated plot}\end{array}\right) - \left(\begin{array}{c}\text{Degree of damage in}\\\text{treated plot}\end{array}\right)}{\text{Degree of damage in untreated plot}}$$

The results are shown in Table 6 wherein the commercially available fungicide is a 3.0% solution of polyoxin PS.

Table 6

| Compound No. | Concentration (ppm) | Degree of damage (%) | Degree of disease-preventing effect | Chemical injury |
| --- | --- | --- | --- | --- |
| 1 | 500 | 0 | 100 | None |
| 2 | 500 | 0 | 100 | '' |
| 3 | 500 | 0 | 100 | '' |
| 4 | 500 | 0 | 100 | '' |
| 5 | 500 | 0 | 100 | '' |
| 6 | 500 | 0 | 100 | '' |
| 9 | 500 | 0 | 100 | '' |
| 15 | 500 | 0 | 100 | '' |
| 20 | 500 | 0 | 100 | '' |
| 21 | 500 | 0 | 100 | '' |
| 22 | 500 | 0 | 100 | '' |
| 24 | 500 | 0 | 100 | '' |
| 30 | 500 | 1.8 | 98 | '' |
| 31 | 500 | 1.8 | 98 | '' |
| 32 | 500 | 0 | 100 | '' |
| 34 | 500 | 0 | 100 | '' |
| 35 | 500 | 0 | 100 | '' |
| 36 | 500 | 0 | 100 | '' |
| 37 | 500 | 0 | 100 | '' |
| 38 | 500 | 0 | 100 | '' |
| 39 | 500 | 0 | 100 | '' |
| 40 | 500 | 0 | 100 | '' |
| 42 | 500 | 3.6 | 94 | '' |
| 46 | 500 | 0 | 100 | '' |
| 47 | 500 | 0 | 100 | '' |
| 48 | 500 | 0 | 100 | '' |
| 49 | 500 | 1.8 | 98 | '' |
| 56 | 500 | 0 | 100 | '' |
| 59 | 500 | 0 | 100 | '' |
| Commercially available fungicide | 1000* | 4.8 | 95 | '' |
| Untreated | — | 100.0 | — | '' |

*1000 fold dilution.

Test 6

Controlling effects on bacterial leaf spot of rice

Two loopfuls of a spore suspension of Xanthomonas oryzae were applied to the second leaf of rice plants cultured in pots of 9 cm in diameter and grown up to the five leaved stage for inoculation. After 24 hours and 48 hours, the test compound in the form of a wettable powder preparation was applied to the plants. On the 7th day from the inoculation, observation was made, and the degree of damage was calculated as in test 5. The results are shown in Table 7 wherein the commercially available fungicide is a 10% wettable powder preparation of phenazin-5-oxide.

Table 7

| Compound No. | Concentration (ppm) | Number of leaves | Degree of damage (%) | Chemical injury |
| --- | --- | --- | --- | --- |
| 7 | 1000 | 30 | 10.0 | None |
| 12 | 1000 | 30 | 10.0 | '' |
| 18 | 1000 | 30 | 16.7 | '' |
| 50 | 1000 | 30 | 13.3 | '' |

Table 7-continued

| Compound No. | Concentration (ppm) | Number of leaves | Degree of damage (%) | Chemical injury |
| --- | --- | --- | --- | --- |
| 51 | 1000 | 30 | 9.6 | '' |
| 58 | 1000 | 30 | 16.7 | '' |
| Commercially available fungicide | 1000* | 30 | 26.7 | '' |
| Untreated | — | 40 | 97.5 | '' |

*1000 fold dilution.

Test 7

Powdery mildew controlling effects

The test compound in the form of an emulsifiable concentrate preparation was applied to seed leaves of cucumbers cultured in pots of 9 cm in diameter and having nipped off the first leaf when developed at a rate of 7 ml of the concentrate per pot by the use of a spray gun. After 24 hours, a spore suspension of Sphaerotheca fuliginea was sprayed on the plants, and the pots were left in a room at 28°C in a humidity of 60 to 80% for 14 days. Then, the infectious state of the seed leaves was observed, and the degree of damage and the degree of disease-preventing effect were calculated according to the following equations, respectively:

$$\text{Degree of damage} = \frac{\Sigma\left(\begin{array}{c}\text{Infectious}\\\text{index}\end{array} \times \begin{array}{c}\text{Number of}\\\text{seed leaves}\end{array}\right)}{\text{Total number of seed leaves} \times 5} \times 100$$

wherein the infectious index was determined by the following criteria:

| Infectious index | Infectious state |
| --- | --- |
| 0 | No infectious spot |
| 1 | Infectious spots only at or around the inoculated place |
| 2 | Infectious spots in about one fifth of the inoculated seed leaf |
| 3 | Infectious spots in about two fifths of the inoculated seed leaf |
| 4 | Infectious spots in about three fifths of the inoculated seed leaf |
| 5 | Infectious spots in four fifths or more of the inoculated seed leaf |

Degree of disease-preventing effect =

$$\frac{\left(\begin{array}{c}\text{No. of infectious}\\\text{spots in untreated plot}\end{array}\right) - \left(\begin{array}{c}\text{No. of infectious}\\\text{spots in treated plot}\end{array}\right)}{\text{Number of infectious spots in untreated plot}} \times 100$$

The results are shown in Table 8 wherein the commercially available fungicide is a 25% wettable powder preparation of S,S-6-methylquinoxaline-2,3-diyldithiocarbonate.

Table 8

| Compound No. | Concentration (ppm) | Degree of damage (%) | Degree of disease-preventing effect | Chemical injury |
| --- | --- | --- | --- | --- |
| 1 | 500 | 0 | 100 | None |
| 2 | 500 | 0 | 100 | '' |
| 3 | 500 | 0 | 100 | '' |
| 4 | 500 | 0 | 100 | '' |
| 5 | 500 | 0 | 100 | '' |
| 6 | 500 | 0 | 100 | '' |
| 7 | 500 | 0 | 100 | '' |
| 8 | 500 | 0 | 100 | '' |

Table 8-continued

| Compound No. | Concentration (ppm) | Degree of damage (%) | Degree of disease-preventing effect | Chemical injury |
|---|---|---|---|---|
| 9 | 500 | 0 | 100 | '' |
| 11 | 500 | 0 | 100 | '' |
| 12 | 500 | 0 | 100 | '' |
| 13 | 500 | 0 | 100 | '' |
| 14 | 500 | 0 | 100 | '' |
| 15 | 500 | 0 | 100 | '' |
| 16 | 500 | 0 | 100 | '' |
| 17 | 500 | 0 | 100 | '' |
| 18 | 500 | 0 | 100 | '' |
| 20 | 500 | 0 | 100 | '' |
| 21 | 500 | 0 | 100 | '' |
| 22 | 500 | 0 | 100 | '' |
| 23 | 500 | 0 | 100 | '' |
| 24 | 500 | 0 | 100 | '' |
| 25 | 500 | 0 | 100 | '' |
| 26 | 500 | 0 | 100 | '' |
| 29 | 500 | 0 | 100 | '' |
| 30 | 500 | 0 | 100 | '' |
| 32 | 500 | 7.6 | 92 | '' |
| 35 | 500 | 7.0 | 93 | '' |
| 36 | 500 | 4.8 | 95 | '' |
| 37 | 500 | 6.6 | 93 | '' |
| 38 | 500 | 7.6 | 92 | '' |
| 39 | 500 | 0 | 100 | '' |
| 41 | 500 | 7.6 | 92 | '' |
| 42 | 500 | 4.0 | 96 | '' |
| 44 | 500 | 7.6 | 92 | '' |
| 46 | 500 | 4.8 | 95 | '' |
| 47 | 500 | 1.7 | 98 | '' |
| 48 | 500 | 2.6 | 97 | '' |
| 49 | 500 | 0 | 100 | '' |
| 50 | 500 | 9.2 | 91 | '' |
| 51 | 500 | 4.8 | 95 | '' |
| 53 | 500 | 6.6 | 93 | '' |
| 54 | 500 | 1.7 | 98 | '' |
| 55 | 500 | 6.6 | 93 | '' |
| 56 | 500 | 7.6 | 92 | '' |
| 57 | 500 | 0 | 100 | '' |
| 58 | 500 | 4.8 | 95 | '' |
| 59 | 500 | 6.6 | 93 | '' |
| 60 | 500 | 0 | 100 | '' |
| Commercially available fungicide | 200 | 10.8 | 87 | '' |
| Untreated | — | 100.0 | — | '' |

Test 8

Controlling effects on anthracnose of cucumber

The test compound in the form of an emulsifiable concentrate preparation was applied to the seed leaves of cucumbers cultured in pots of 9 cm in diameter at a rate of 7 ml per pot by the aid of a spray gun. After 24 hours, a spore suspension of Colletotrichum lagenarium cultured on potato agar medium was sprayed on the plants, and the pots were left in a room at 20°C in a humidity of 95%. Five days thereafter, the infectious state of the seed leaves was observed, and the degree of damage and the degree of disease-preventing effect were calculated as in Test 7.

The results are shown in Table 9 wherein the commercially available fungicide is a 80% wettable powder preparation of N-trichloromethylthio-4-cyclohexene-1,2-dicarboximide.

Table 9

| Compound No. | Concentration (ppm) | Degree of damage (%) | Degree of disease-preventing effect | Chemical injury |
|---|---|---|---|---|
| 1 | 200 | 0 | 100 | None |
| 3 | 200 | 0 | 100 | '' |
| 5 | 200 | 0 | 100 | '' |
| 7 | 200 | 1.9 | 98 | '' |
| 9 | 200 | 0 | 100 | '' |
| 10 | 200 | 0 | 100 | '' |
| 12 | 200 | 0 | 100 | '' |
| 13 | 200 | 0 | 100 | '' |
| 14 | 200 | 0 | 100 | '' |
| 15 | 200 | 0 | 100 | '' |
| 17 | 200 | 0 | 100 | '' |
| 19 | 200 | 0 | 100 | '' |
| 21 | 200 | 0 | 100 | '' |
| 23 | 200 | 1.9 | 98 | '' |
| 24 | 200 | 0 | 100 | '' |
| 25 | 200 | 3.8 | 96 | '' |
| 26 | 200 | 0 | 100 | '' |
| 27 | 200 | 7.6 | 92 | '' |
| 28 | 200 | 1.9 | 98 | '' |
| 29 | 200 | 5.7 | 94 | '' |
| 30 | 200 | 0 | 100 | '' |
| 31 | 200 | 0 | 100 | '' |
| 33 | 200 | 3.8 | 96 | '' |
| 35 | 200 | 3.8 | 96 | '' |
| 36 | 200 | 1.9 | 98 | '' |
| 40 | 200 | 0 | 100 | '' |
| 41 | 200 | 0 | 100 | '' |
| 43 | 200 | 1.9 | 98 | '' |
| 44 | 200 | 0 | 100 | '' |
| 45 | 200 | 0 | 100 | '' |
| 48 | 200 | 0 | 100 | '' |
| 49 | 200 | 0 | 100 | '' |
| 50 | 200 | 3.8 | 96 | '' |
| 51 | 200 | 0 | 100 | '' |
| 52 | 200 | 1.9 | 98 | '' |
| 53 | 200 | 1.9 | 98 | '' |
| 57 | 200 | 0 | 100 | '' |
| 60 | 200 | 3.8 | 96 | '' |
| Commercially available fungicide | 200 | 25.6 | 73 | '' |
| Untreated | — | 98.2 | — | '' |

Test 9

Cucumber bacterial blight controlling effects

In pots of 9 cm in diameter, field soil was filled, and soil infected with Rhizoctonia solani was placed thereon in an amount of 10 ml per pot. The test compound in a wettable powder preparation was diluted with water and poured in the pots at a rate of 9 ml per pot. After 4 hours, ten seeds of cucumber were sowed in each pot. Five days thereafter, the infectious state was observed, and the percentage of healthy seedlings was calculated according to the following equation:

Percentage of healthy seedlings (%)
$$= \frac{\text{Number of healthy seedlings in treated plot}}{\text{Number of healthy seedlings in non-inoculated and untreated plot}} \times 100$$

The results are shown in Table 10 wherein the commercially available fungicide is pentachloronitrobenzene.

Table 10

| Compound No. | Concentration (ppm) | Percentage of healthy seedlings (%) | Chemical injury |
|---|---|---|---|
| 1 | 500 | 100.0 | None |
| 2 | 500 | 90.0 | '' |
| 3 | 500 | 100.0 | '' |
| 4 | 500 | 100.0 | '' |
| 5 | 500 | 86.7 | '' |
| 7 | 500 | 100.0 | '' |
| 8 | 500 | 90.0 | '' |
| 16 | 500 | 93.4 | '' |

Table 10-continued

| Compound No. | Concentration (ppm) | Percentage of healthy seedlings (%) | Chemical injury |
|---|---|---|---|
| 20 | 500 | 86.7 | '' |
| 22 | 500 | 100.0 | '' |
| 31 | 500 | 100.0 | '' |
| 32 | 500 | 86.7 | '' |
| 34 | 500 | 100.0 | '' |
| 46 | 500 | 93.4 | '' |
| 47 | 500 | 86.7 | '' |
| 54 | 500 | 93.4 | '' |
| 55 | 500 | 90.0 | '' |
| 57 | 500 | 93.4 | '' |
| Commercially available fungicide | 500 | 76.7 | '' |
| Untreated | — | 96.7 | '' |

Test 10

Fusarium wilt controlling effects

In pots of 9 cm in diameter, field soil was filled, and soil infected with Fusarium oxysporum f. raphani was placed thereon in an amount of 10 ml per pot. The test compound in a wettable powder preparation was diluted with water and poured in the pots at a rate of 18 ml per pot. Then, 20 seeds of radish were sowed in each pot. After 3 weeks, the infectious state was observed, and the percentage of healthy seedlings was calculated as in Test 9.

The results are shown in Table 11 wherein the commercially available fungicide is a 80% wettable powder preparation of N-trichloromethylthio-4-cyclohexene-1,2-dicarboximide.

Table 11

| Compound No. | Concentration (ppm) | Percentage of healthy seedlings (%) | Chemical injury |
|---|---|---|---|
| 1 | 500 | 100.0 | None |
| 3 | 500 | 88.7 | '' |
| 4 | 500 | 100.0 | '' |
| 5 | 500 | 100.0 | '' |
| 6 | 500 | 94.4 | '' |
| 9 | 500 | 90.8 | '' |
| 10 | 500 | 100.0 | '' |
| 11 | 500 | 100.0 | '' |
| 12 | 500 | 94.4 | '' |
| 18 | 500 | 94.4 | '' |
| 24 | 500 | 100.0 | '' |
| 47 | 500 | 98.0 | '' |
| 52 | 500 | 88.7 | '' |
| 53 | 500 | 88.7 | '' |
| 58 | 500 | 98.0 | '' |
| 60 | 500 | 94.4 | '' |
| Commercially available fungicide | 500 | 72.0 | '' |
| Untreated | — | 100.0 | '' |

What is claimed is:

1. A phenylenediamine compound of the formula:

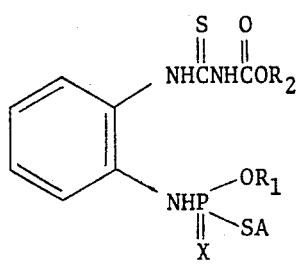

wherein $R_1$ is a lower alkyl group, $R_2$ is a lower alkyl group, A is a lower alkyl group, a lower alkenyl group, a lower alkynyl group, a halo(lower)alkyl group, a cyano(lower)alkyl group, a lower alkylthio(lower)alkyl group, a halo(lower)alkenyl group, a lower alkoxy(lower)alkyl group, a lower alkoxycarbonyl(lower)alkyl group, a lower alkylcarbamoyl(lower)alkyl group, a phenyl group or a phenyl(lower)alkyl group having one to three substituents on the benzene ring, said substituents being lower alkyl, lower alkoxy, nitro, halogen or lower alkylenedioxy, and X is an oxygen atom or a sulfur atom.

2. A phenylenediamine compound of the formula:

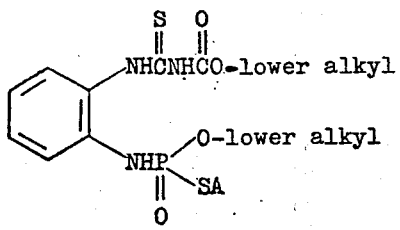

wherein A is lower alkyl.

3. A phenylenediamine compound of the formula:

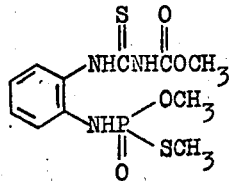

4. A phenylenediamine compound of the formula:

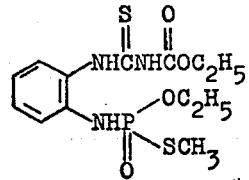

5. A phenylenediamine compound of the formula:

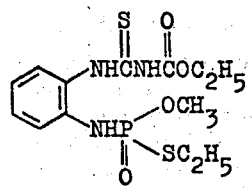

6. a phenylenediamine compound of the formula:

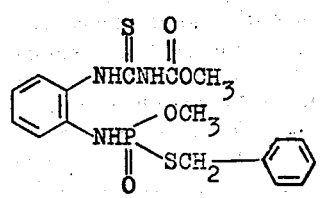

7. A phenylenediamine compound of the formula:

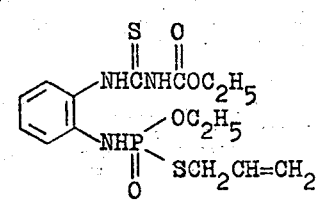

* * * * *